(12) United States Patent
Platteeuw et al.

(10) Patent No.: US 10,525,099 B2
(45) Date of Patent: Jan. 7, 2020

(54) ORALLY DISINTEGRATING SOLID PHARMACEUTICAL DOSAGE UNIT CONTAINING A PARTUS CONTROL SUBSTANCE

(71) Applicant: Oxytone Bioscience B.V., Zeist (NL)

(72) Inventors: Johannes Jan Platteeuw, Boxtel (NL); Herman Jan Tijmen Coelingh Bennink, Zeist (NL)

(73) Assignee: OXYTONE BIOSCIENCE B.V., Zeist (NL)

( * ) Notice: Subject to any disclaimer, the term of this patent is extended or adjusted under 35 U.S.C. 154(b) by 62 days.

(21) Appl. No.: 15/516,078

(22) PCT Filed: Sep. 29, 2015

(86) PCT No.: PCT/NL2015/050674
§ 371 (c)(1),
(2) Date: Mar. 31, 2017

(87) PCT Pub. No.: WO2016/053092
PCT Pub. Date: Apr. 7, 2016

(65) Prior Publication Data
US 2017/0304393 A1     Oct. 26, 2017

(30) Foreign Application Priority Data

Oct. 1, 2014   (EP) ..................................... 14187346

(51) Int. Cl.
| | |
|---|---|
| *A61K 38/095* | (2019.01) |
| *A61K 38/08* | (2019.01) |
| *A61K 9/00* | (2006.01) |
| *A61K 9/20* | (2006.01) |
| *A61K 47/12* | (2006.01) |
| *A61K 47/36* | (2006.01) |

(52) U.S. Cl.
CPC .......... *A61K 38/095* (2019.01); *A61K 9/0056* (2013.01); *A61K 9/205* (2013.01); *A61K 38/08* (2013.01); *A61K 47/12* (2013.01); *A61K 47/36* (2013.01)

(58) Field of Classification Search
None
See application file for complete search history.

(56) References Cited

U.S. PATENT DOCUMENTS

| | | | | |
|---|---|---|---|---|
| 4,754,597 | A * | 7/1988 | Buxton ................. | A01N 25/34 34/287 |
| 8,920,819 | B2 * | 12/2014 | Uchegbu .......... | A61K 47/48907 424/400 |

FOREIGN PATENT DOCUMENTS

| | | |
|---|---|---|
| AT | 251762 B | 1/1967 |
| CN | 102580057 A | 7/2012 |
| CN | 104055732 A | 9/2014 |
| GB | 1 437 138 A | 5/1976 |
| WO | WO-91/03233 A1 | 3/1991 |
| WO | WO-2004/026279 A1 | 4/2004 |
| WO | WO-2007/025249 A2 | 3/2007 |
| WO | WO-2010/030180 A2 | 3/2010 |
| WO | WO-2012/042371 A2 | 4/2012 |

OTHER PUBLICATIONS

"Heat-stable sublingual oxytocin for the prevention and treatment of postpartum hemorrhage", Path, May 2014, XP055173819, retrieved from the Internet: URL:http://www.path.org/publications/files/TS_update_sublingual_oxytocin.pdf.
"Heat-stable oxytocin technology opportunity assessment prepared for the Merk for mothers program", Path, Mar. 2013, XP055173807, retrieved from the Internet: URL:http://sites.path.org/mnhtech/files/2013/03/HS1_18March2013.FINAL.pdf.
Ashigbie, "Background paper 6.16 postpartum haemorrhage", Priority Medicines for Europe and the World "A Public Health Approach to Innovation", Jan. 2013, XP055127881, retrieved from the Internet: URL:http://www.who.int/medicines/areas/priority_medicines/BP6_16PPH.pdf.
De Groot et al., "Stability of oral oxytocics in tropical climates", World Health Organization, Ergot Task Group, 1994, 59 pages.
International Search Report issued in International Patent Application No. PCT/NL2015/050673, dated Feb. 16, 2016.
International Search Report issued in International Patent Application No. PCT/NL2015/050674, dated Feb. 16, 2016.
Metia et al., "In vitro and in vivo evaluation of a novel mucoadhesive buccal oxytocin tablet prepared with *Dillenia indica* fruit mucilage", Die Pharmazie, Apr. 2008, vol. 4, 270-274.
Sun et al., "Effect of dextran molecular weight on protein stabilization during freeze-drying and storage", CryoLetters, 2001, vol. 22, pp. 285-292.
Wang, Lyophilization and development of solid protein pharmaceuticals, International Journal of Pharmaceuticals, 2000, vol. 203, pp. 1-60.

(Continued)

*Primary Examiner* — David J Blanchard
*Assistant Examiner* — Daniel F. Coughlin
(74) *Attorney, Agent, or Firm* — Gilberto M. Villacorta; Sunit Talapatra; Foley & Lardner LLP

(57) ABSTRACT

The present invention provides an orally disintegrating solid pharmaceutical dosage unit having a weight between 50 and 1,000 mg, said dosage unit consisting of: 1-100 wt. % of particles consisting of: 0.01-10 wt. % of a partus control substance selected from oxytocin, carbetocin, atosiban and combinations thereof; 5-70 wt. % of buffering agent; 20-94 wt. % of branched glucan; 0-70 wt. % of other pharmaceutically acceptable ingredients; 0-95 wt. % of one or more pharmaceutically acceptable excipients; the solid dosage unit comprising at least 5 µg of the partus control substance and having a pH buffer range of 3.5-5.7. The solid dosage unit of the present invention is easy to manufacture and perfectly suited for sublingual, buccal or sublabial administration. Furthermore, the dosage unit does not need to be stored and distributed under temperature controlled conditions.

14 Claims, No Drawings

(56) References Cited

OTHER PUBLICATIONS

Avanti et al., "A new strategy to stabilize oxytocin in aqueous solutions: I. the effects of divalent metal ions and citrate buffer", The AAPS Journal, Jun. 2011, vol. 13, No. 2, pp. 284-290.
Avanti et al., "Aspartate buffer and divalent metal ions affect oxytoxin in aqueous solution and protect it from degradation", Int. J. Pharm, Feb. 2013, vol. 444, pp. 139-145.
De Groot et al., "Bioavailability and pharmacokinetics of sublingual oxytocin in male volunteers", J. of Pharm. Pharmacol., 1995, vol. 47, pp. 571-575.
De Groot et al., "Oxytocin and desamino-oxytocin tablets are not stable under simulated tropical conditions", J. of Clinical Pharmacy and Therapeutics, 1995, vol. 20, pp. 115-119.
Hawe et al., "Towards heat-stable oxytocin formulations: analysis of degradation kinetics and identification of degradation products", Pharm. Res., Jul. 2009, vol. 26, No. 7, pp. 1679-1688.

\* cited by examiner

US 10,525,099 B2

ORALLY DISINTEGRATING SOLID PHARMACEUTICAL DOSAGE UNIT CONTAINING A PARTUS CONTROL SUBSTANCE

CROSS-REFERENCE TO RELATED APPLICATIONS

This application is the National Phase of International Patent Application No. PCT/NL2015/050674, filed Sep. 29, 2015, published on Apr. 7, 2016 as WO 2016/053092 A1, which claims priority to European Patent Application No. 14187346.3, filed Oct. 1, 2014. The contents of these applications are herein incorporated by reference in their entirety.

TECHNICAL FIELD OF THE INVENTION

The present invention provides an orally disintegrating solid pharmaceutical dosage unit having a weight between 50 and 1,000 mg, said dosage unit consisting of:
  1-100 wt. % of particles consisting of:
    0.01-10 wt. % of a partus control substance selected from oxytocin, carbetocin, atosiban and combinations thereof;
    5-70 wt. % of buffering agent;
    20-94 wt. % of branched glucan;
    0-70 wt. % of other pharmaceutically acceptable ingredients;
  0-99 wt. % of one or more pharmaceutically acceptable excipients;
the solid dosage unit comprising at least 5 µg of the partus control substance and having a pH buffer range of 3.5-5.7.

The solid dosage units of the present invention are particularly suited for sublingual, buccal or sublabial administration of the partus control substance.

The invention also provides the use of these solid dosage units in medical treatments, wherein the treatment comprises buccal, sublingual or sublabial administration of the solid dosage unit. The solid dosage unit is particularly suited for use in the treatment of postpartum hemorrhage.

BACKGROUND OF THE INVENTION

Oxytocin is a mammalian hormone, secreted by the posterior pituitary gland, that acts primarily as a neuromodulator in the brain. Oxytocin plays an important role in the neuroanatomy of intimacy, specifically during and after childbirth. It is released in large amounts after distension of the cervix and uterus during labour, facilitating childbirth, maternal bonding and lactation.

Oxytocin is a peptide of nine amino acids (a nonapeptide). Its systematic name is cysteine-tyrosine-isoleucine-glutamine-asparagine-cysteine-proline-leucine-glycine-amide. Its half-life in the blood is typically about three minutes. Oxytocin has a molecular mass of 1007.19 g/mol. One international unit (IU) of oxytocin is the equivalent of about 1.68 micrograms of pure peptide.

Oxytocin as a drug is often used to induce labour and support labour in case of non-progression of parturition and to treat obstetric hemorrhage. Obstetric hemorrhage is estimated to cause 25% of all maternal deaths and is the leading direct cause of maternal mortality worldwide. Postpartum hemorrhage (PPH), defined as vaginal bleeding in excess of 500 ml after delivery, accounts for most cases of obstetric hemorrhage. It occurs in more than 10% of all births and is associated with a 1% case fatality rate.

Although active management of the third stage of labour (AMTSL) can prevent up to 60% of PPH cases, PPH continues to have a devastating impact on women in low-resource settings where home births are common and health care facilities are often inaccessible. Obstetric hemorrhage accounts for 34% of maternal deaths in Africa, 31% in Asia, and 21% in Latin America and the Caribbean. Among women who do survive PPH, approximately 12% will have severe anemia. Also, women who survive severe PPH (greater than 1,000 ml of blood loss) are significantly more likely to die during the following year.

Injectable oxytocin (intravenously or intramuscularly) has been recommended by the World Health Organization (WHO) for routine use during AMTSL and is the preferred drug for the prevention and management of blood loss after childbirth. Administering the injection, however, requires skill, sterilized equipment, and proper disposal of medical waste. Oral administration of oxytocin is not a suitable route of administration, since the peptide oxytocin is degraded in the gastrointestinal tract.

At present, oxytocin is available only as a liquid formulation in single-dose vials of 10 IU for intramuscular (IM) or intravenous (IV) injection. Four other preparations under investigation are at various stages of development and introduction (Uterotonic Research and Policy Agenda for Reducing Mortality and Morbidity Related to Postpartum Hemorrhage. A consensus statement issued by the participants in the meeting on "The Role of Uterotonics in Reducing Postpartum Hemorrhage: What Next?", held on 4-5 Oct. 2011 in The Hague, The Netherlands). These preparations are:
a) oxytocin delivered IM via a Uniject® device packaged with a Time Temperature Indicator (TTI);
b) a more heat-stable liquid oxytocin formulation;
c) lyophilized heat-stable oxytocin reconstituted with sterile water for IM or IV injection;
d) a heat-stable powdered oxytocin formulation for aerosol delivery and inhalation.

In 1993 and 1994, WHO-supported studies demonstrated that oxytocin loses potency in field conditions, particularly tropical climates. Depending on the manufacturer and regulatory agency specification, all oxytocin products must be stored in either controlled room temperature (25° C. or lower) or refrigerated storage (2° C. to 8° C.) to ensure quality.

In third world countries, it is often practically and/or economically impossible to protect pharmaceutical preparations from the harmful effects of high temperatures and high humidity during transportation, storage and use. Besides stability in high temperature and humidity conditions, pharmaceutical preparations for use in tropical climates must fulfill extra requirements, such as a simple route of administration and untrained people should be able to administer the pharmaceutical preparation safely.

Carbetocin is a long-acting synthetic octapeptide having an action very similar to oxytocin. Carbetocin is also used as an obstetric drug to control postpartum hemorrhage and bleeding after giving birth. The commercially available carbetocin formulation PABAL® (100 µg/ml solution for injection, Ferring Pharmaceuticals Ltd.) is not stable at room temperature and requires refrigerated storage at a temperature of 2-8° C.

Atosiban is a synthetic nonapeptide and is an inhibitor of oxytocin and vasopressin. It is used as an intravenous medication as a labour repressor (tocolytic) to halt premature labour. Atosiban is available as a lyophilized (freeze dried) powder that should be stored desiccated below −18° C. At room temperature lyophilized atosiban is stable for 3 weeks.

Recently a lot of scientific research has been performed to study what causes the degradation of oxytocin in aqueous solutions.

Hawe et al. (Pharm Res. 2009 July; 26(7): 1679-1688) observed that the degradation of oxytocin strongly depends on the pH of the formulation, with the highest stability at pH 4.5.

Recent studies describe new strategies to stabilize oxytocin in aqueous solutions. Avanti et al. (The AAPS Journal. 2011; 13(2):284-290) and Avanti et al. (Int J Pharm. 2013 Feb. 28; 444(1-2):139-45) suggested that stability of oxytocin in aqueous solution can be improved by addition of divalent metal ions in combination with a citrate or aspartate buffer, respectively.

WO 2010/030180 mentions that the stability of aqueous peptide formulations, containing small therapeutic Cys-containing peptides such as oxytocin, is greatly enhanced by the presence of a buffer and at least one non-toxic source of divalent metal ions in a concentration of at least 2 mM.

WO 2012/042371 describes a pharmaceutical liquid composition, comprising carbetocin or pharmaceutically active salt thereof, and having pH between 5.0 and 6.0. This liquid composition may be stored at room temperature (e.g. at 25° C. and 60% relative humidity) for a sustained period (e.g. up to 2 years). The examples of the international patent application described liquid aqueous formulations containing carbetocine, buffer and anti-oxidant (methionine and/or EDTA).

A recent publication (http://path.org/publications/files/TS_oxytocin_fdt_for_pph_pos.pdf) describes a proposal for a project that aims to develop a heat-stable, fast-dissolving oxytocin tablet for sublingual administration. Several potential advantages of such a sublingual oxytocin tablet vis-à-vis existing oxytocin preparations for intramuscular injection or intravenous infusion are listed.

Sublingual tablets containing oxytocin have been marketed in the past (brand names Pitocin® and Syntocinon®). These products have been withdrawn from the market as greater control in induction and augmentation of labour could be achieved by intravenous or intramuscular administration of oxytocin. Sublingual administration was considered to be more unpredictable and in addition the pharmacokinetic profile showed an unfavorable latent period. Also, the sublingual tablets were not stable enough under tropical conditions.

De Groot et al. (J. of Pharm. Pharmacol. 1995, 47; 571-575) describe a study in which bioavailability and pharmacokinetics of sublingual oxytocin (Pitocin® tablet) was investigated. The study showed substantial inter-individual variability in bioavailability of oxytocin. The authors conclude that sublingual administration of oxytocin does not seem a reliable route for immediate prevention of PPH due to 'long' lag time and 'long' absorption half-life.

De Groot et al. (J. of Clinical Pharmacy and Therapeutics, 1995, 20, 115-119) describe experiments wherein the effect of simulated tropical conditions on buccal oxytocin tablets (tablet components not specified) was studied. The conclusion was that tropical conditions make oxytocin tablets unstable, with humidity as the most adverse factor. The oxytocin tablets were partially protected from the harmful effect of humidity by sealed aluminum package.

There remains a need for an oxytocin formulation for in-mouth (e.g. sublingual or buccal) administration that has good bioavailability and pharmacokinetics, that does not require refrigerated storage, that can be administered by untrained people and that can be manufactured and distributed at low cost. This same need exists for carbetocin and atosiban, especially since currently formulations for in-mouth administration of carbetocin or atosiban are not commercially available.

SUMMARY OF THE INVENTION

The present invention provides an orally disintegrating solid pharmaceutical dosage unit containing a partus control substance (PCS) that meets the aforementioned desiderata. More particularly, the present invention relates to an orally disintegrating solid pharmaceutical dosage unit having a weight between 50 and 1,000 mg, said dosage unit consisting of:
  1-100 wt. % of particles consisting of:
    0.01-10 wt. % of a partus control substance selected from oxytocin, carbetocin, atosiban and combinations thereof;
    5-70 wt. % of buffering agent;
    20-94 wt. % of branched glucan;
    0-70 wt. % of other pharmaceutically acceptable ingredients;
  0-99 wt. % of one or more pharmaceutically acceptable excipients;
the solid dosage unit comprising at least 5 µg of the partus control substance and having a pH buffer range of 3.5-5.7.

The solid dosage unit of the present invention is easy to manufacture and perfectly suited for sublingual, buccal or sublabial administration. Furthermore, the dosage unit does not need to be stored and distributed under temperature controlled conditions.

DETAILED DESCRIPTION OF THE INVENTION

A first aspect of the invention relates to an orally disintegrating solid pharmaceutical dosage unit having a weight between 50 and 1,000 mg, said dosage unit consisting of:
  1-100 wt. % of particles consisting of:
    0.01-10 wt. % of a partus control substance (PCS) selected from oxytocin, carbetocin, atosiban and combinations thereof;
    5-70 wt. % of buffering agent;
    20-94 wt. % of branched glucan;
    0-70 wt. % of other pharmaceutically acceptable ingredients;
  0-99 wt. % of one or more pharmaceutically acceptable excipients;
the solid dosage unit comprising at least 5 µg of the partus control substance and having a pH buffer range of 3.5-5.7.

The term 'partus control substance' as used herein refers to a pharmaceutical substance that is capable of repressing progression of partus, of inducing partus or of suppressing or preventing postpartum hemorrhage.

The term 'oxytocin' as used herein refers to oxytocin as well as pharmaceutically acceptable salts thereof.

The term 'carbetocin' as used herein refers to carbetocin as well as pharmaceutically acceptable salts thereof.

The term 'atosiban' as used herein refers to atosiban as well as pharmaceutically acceptable salts thereof.

The term 'buffering agent' as used herein refers to substances that can be used in aqueous systems to drive a solution to a certain pH (e.g. a pH within the range of 3.5-5.7) and that prevents a change in this pH. Buffering agents can be either the weak acid or weak base that would comprise a buffer solution (an aqueous solution comprising a mixture of a weak acid and its conjugate base or a weak base and its conjugate acid). Buffering agents are the substances that are responsible for the buffering seen in buffer solutions. Buffering agents are similar to buffer solutions in that buffering agents are the main components of buffer solutions. They both regulate the pH of a solution and resist changes in pH.

The term 'glucan' as used herein refers to a polysaccharide that is composed of repeating glucose units. The term 'glucan' encompasses both α-glucans and β-glucans. The term 'glucan' also encompassed glucans that have undergone partial hydrolysis.

The term 'branched glucan' as used herein refers to a glucan comprising a straight chain of glycosidically linked glucose molecules and branches of glycosidically linked glucose molecules that are linked to the aforementioned straight chain.

The term 'dextran' as used herein refers to a branched glucan with a straight chain of α-1,6 glycosidically linked glucose molecules and branches beginning from α-1,3 linkages. Dextran is synthesized from sucrose by certain lactic-acid bacteria, the best-known being *Leuconostoc mesenteroides* and *Streptococcus mutans*.

The term 'disulfide bond' as used herein, unless indicated otherwise, refers to a disulfide bond between two amino acid residues, for instance, a disulfide bond between two cystein residues.

The term 'medical treatment' as used herein encompasses both therapeutic and prophylactic treatment.

The term 'sublingual' as used herein refers to the pharmacological route of administration by which a pharmacologically active compound diffuses into the blood through tissues under the tongue.

The term 'buccal' as used herein refers to the pharmacological route of administration by which a pharmacologically active compound diffuses into the blood through tissues of the buccal vestibule, the area inside the mouth between the lining of cheek (the buccal mucosa) and the teeth/gums.

The term 'sublabial' as used herein refers to the pharmacological route of administration by which a pharmacologically active compound is placed between the lip and the gingiva and diffuses from there into the blood.

Examples of solid dosage units encompassed by the present invention include tablets, dragees, lozenges and films. In accordance with a preferred embodiment, the dosage unit is a tablet, most preferably a compressed tablet.

The solid dosage unit typically has a weight between 60 and 900 mg, more preferably between 70 and 500 mg, even more preferably between 75 and 300 mg and most preferably between 80 and 200 mg.

The PCS containing particles preferably have a volume weighted average size between 5 and 200 μm, more preferably between 20 and 150 μm and most preferably between 50 and 100 μm.

The PCS containing particles preferably represent 1-30 wt. %, more preferably 2-20 wt. %, even more preferably 3-15 wt. % and most preferably 4-12.5 wt. % of the solid dosage unit, the remainder of the dosage unit consisting of one or more pharmaceutically acceptable excipients.

In one embodiment of the invention the PCS containing particles in the solid dosage unit contain 0.1-9 wt. %, more preferably 0.2-9 wt. %, even more preferably 0.3-8.5 wt. % and most preferably 0.5-8 wt. % of oxytocin.

The solid dosage unit of the present invention typically contains oxytocin in an amount of 40-600 μg, more preferably 80-500 μg, even more preferably 100-450 μg and most preferably 150-400 μg.

In accordance with another embodiment, the PCS containing particles in the solid dosage unit contain 0.2-10 wt. %, more preferably 0.5-9.5 wt. %, even more preferably 1-9 wt. % and most preferably 2-8.5 wt. % of carbetocine.

The solid dosage unit of the present invention typically contains carbetocin in an amount of 100-5,000 μg, more preferably 200-4,000 μg, even more preferably 300-3,000 μg and most preferably 400-2,500 μg.

In a preferred embodiment the PCS is oxytocin. In another preferred embodiment the PCS is carbetocin. In another preferred embodiment the PCS is atosiban.

The solid dosage unit preferably has a pH buffer range of 4.0 to 5.5, more preferably of 4.2 to 5.2. The pH buffer range of the solid dosage unit is determined by dispersing 1 g of the solid dosage unit in 10 ml of distilled water at 20° C. and measuring the pH after all soluble components of the dosage unit have dissolved in the water. The buffering agent is preferably contained in the PCS containing particles in a concentration of 0.5-20 mmol/g, more preferably of 0.8-15 mmol/g and most preferably of 1-10 mmol/g.

In a preferred embodiment, the PCS containing particles contain 6-60 wt. % of buffering agent, more preferably 7-45 wt. % and most preferably of 8-35 wt. % of buffering agent.

The buffering agent in the PCS containing particles preferably has a pH buffer range of 4.0 to 5.5, more preferably of 4.2 to 5.2. The pH buffer range of a buffering agent can be determined by dissolving 1 g of the buffering agent in 10 ml of distilled water at 20° C. and measuring the pH after all soluble components of the dosage unit have dissolved in the water.

The buffering agent in the PCS containing particles is preferably selected from citrate, acetate, aspartate and combinations thereof. The term 'citrate', unless indicated otherwise, encompasses both fully protonated citric acid as well as salts of citric acid. The same holds, *mutatis mutandis*, for other buffering agents.

The branched glucan is preferably contained in the PCS containing particles in a concentration of 5-93 wt. %, more preferably of 10-92 wt. %, even more preferably of 20-90 wt. % and most preferably 35-80 wt. %.

Examples of branched glucans that may be employed in accordance with the present invention include dextran, glycogen, amylopectin and combinations thereof. Preferably, the branched dextran employed is an α-glucan. Most preferably, the branched glucan employed is dextran.

In a particularly preferred embodiment the branched glucan is a hydrolyzed dextran. The hydrolyzed dextran has an average molecular weight between 10-2000 kDa, more preferably between 10-1000 kDa, even more preferably between 10-500 kDa and most preferably between 10-200 kDa.

Besides the PCS, the buffering agent and the branched glucan, the particles of the dosage unit may optionally contain up to 70 wt. %, more preferably up to 60 wt. % and most preferably up to 30 wt. % of one or more other pharmaceutically acceptable ingredients.

The one or more other pharmaceutically acceptable ingredients that are optionally contained in the PCS containing particles include a wide variety of pharmaceutically acceptable ingredients, such as divalent metal cations, polysaccharides (other than branched glucan), proteins, redox reagents, sequestrants, sugar alcohols, sugars and combinations thereof. The term 'polysaccharides' includes modified polysaccharides such as, for instance, hydroxypropylmethylcellulose and maltodextrin.

In accordance with a preferred embodiment, the PCS containing particles contain 0.02-10 wt. % of divalent metal cation, more preferably 0.1-8 wt. % and most preferably of 0.5-6 wt. % of divalent metal cation.

In accordance with a preferred embodiment of the present invention, the divalent metal cation and the PCS are present in the particles of the solid dosage unit in a molar ratio between 1:1 and 1000:1, more preferably in a molar ratio between 2:1 and 300:1 and most preferably in a molar ratio between 4:1 and 100:1.

The divalent metal cation employed in the PCS containing particles is preferably selected from $Mg^{2+}$, $Ca^{2+}$, $Cu^{2-}$, $Zn^{2+}$ and combinations thereof. More preferably, the divalent metal cation is selected from $Zn^{2+}$, $Ca^{2+}$ and combinations thereof. Most preferably, the divalent metal cation is $Zn^{2+}$.

In accordance with a preferred embodiment, the PCS containing particles contain 0.01-10 wt. % of a sequestrant, more preferably contain 0.05-5 wt. % of sequestrant, most preferably contain 0.08-1 wt. % sequestrant.

The sequestrant employed in the PCS containing particles is preferably EDTA.

According to another preferred embodiment, the PCS containing particles contain 0.01-10 wt. % of redox reagent. More preferably, said particles contain between 0.25-7.5 wt. % of redox reagent, most preferably between 0.5-5 wt. % of redox reagent.

The redox reagent typically is a small molecule compound, with a molecular weight generally less than about 1000 g/mol, preferably less than about 500 g/mol.

In accordance with one embodiment, the redox agent is an oxidant that is capable of promoting the oxidative conversion of thiol groups into disulfide bonds. Examples of such oxidants include ascorbic acid, ascorbic acid derivatives (e.g. ascorbate esters), iodate, bromate and persulfate.

In accordance with another embodiment, the redox agent comprises at least one thiol (SH) functional group which can act as a reducing or oxidizing agent for disulfide bonds, thiols, or thiolate species present in the PCS and thereby moderate disulfide exchange reactions between peptides. Preferred examples include dithiothreitol, mercaptoethanol, cysteine, homocysteine, methionine, and glutathione (reduced).

Examples of pharmaceutically acceptable excipients that may be employed in the solid dosage unit of the present invention besides the PCS containing particles include lactose, mannitol, xylitol, microcrystalline cellulose, croscarmellose sodium and combinations thereof.

The solid dosage units of the present invention can be packaged in different ways. Preferably, the dosage units are packaged in a blister pack containing at least 5 dosage units.

Another aspect of the invention relates to the use of the present dosage unit in medical treatment, wherein the treatment comprises buccal, sublingual or sublabial administration of said dosage unit. Preferably, the dosage unit is used in medical treatment of a mammal, most preferably a human.

According to a particularly preferred embodiment, the dosage unit contains at least 2 µg of oxytocin and is used in the treatment of postpartum hemorrhage, said treatment comprising buccal, sublingual or sublabial administration of said dosage unit. Even more preferably, the dosage unit is administered in an amount to provide at least 10 µg oxytocin, most preferably 15-400 µg oxytocin.

According to another preferred embodiment, the dosage unit contains at least 10 µg of carbetocin and is used in the treatment of postpartum hemorrhage, said treatment comprising buccal, sublingual or sublabial administration of said dosage unit. Even more preferably, the dosage unit is administered in an amount to provide at least 100 µg carbetocin, most preferably 200-2000 µg carbetocin.

According to yet another preferred embodiment, the dosage unit contains at least 5 µg, more preferably at least 10 µg of atosiban and is used to prevent or halt premature labour, said treatment comprising buccal, sublingual or sublabial administration of said dosage unit. Even more preferably, the dosage unit is administered in an amount to provide at least 100 µg atosiban, most preferably 1,000-75,000 µg atosiban.

Yet another aspect of the invention relates to a method of preparing a solid dosage unit as described above, said method comprising the steps of:
  providing an aqueous solution comprising the partus control substance, the buffering agent, branched glucan and optionally one or more other pharmaceutically acceptable ingredients;
  removing water from the aqueous solution, optionally after having sprayed the aqueous solution onto carrier particles, to produce solid particles containing the partus control substance, the buffering agent, the branched glucan and the optionally one or more other pharmaceutically acceptable ingredients;
  mixing the particles with the one or more pharmaceutically acceptable excipients; and
  forming the mixture into a solid dosage unit.

Typically, the aqueous solution has a pH in the range of 3.5 to 5.7, more preferably in the range of 4.0 to 5.5 and most preferably in the range of 4.2 to 5.2 before the water removal.

The water may be removed from the aqueous solution by a variety of methods, including spray drying, freeze drying, vacuum drying, solvent extraction etc.

The one or more pharmaceutically acceptable excipients that are mixed with the particles before the forming of the mixture in a solid dosage unit are pharmaceutically acceptable excipients as defined herein before in relation to the solid dosage unit.

The forming of the mixture of particles and one or more pharmaceutically acceptable excipients into a solid dosage unit preferably comprises compaction of this mixture.

Compactibility is the ability of a powder bed to form a mechanically strong tablet; whereas the compressibility is the ability of a powder bed to be compressed and consequently be reduced in volume. Compaction as applicable to a pharmaceutical powder consists of the simultaneous processes of compression and consolidation of a two-phase (particulate solid-gas) system due to an applied force. Consolidation refers to the increase in the mechanical strength of a material as a result of particle/particle interactions.

The invention is further illustrated by the following non-limiting examples.

EXAMPLES

Example 1

Two 200 ml stock solutions were prepared on the basis of the formulations shown in Table 1. The water used was at room temperature (appr. 20° C.) The solid ingredients, except for the oxytocin, were introduced into a container. Approximately 90% of the required water was added, followed by continuous stirring with a magnetic stirrer until all solids were dissolved. The oxytocin was added and the pH of the solution was set with 1M HCl or 1M NaOH to the required pH value (see Table 1). The remaining amount of water was added and mixed. The solutions were stored at 2-8° C.

TABLE 1

| Ingredients | Stock solution I | Stock solution II |
|---|---|---|
| Citric acid anhydrate | 0.265 g | 0.395 g |
| Sodium citrate dihydrate | 0.805 g | 0.623 g |
| EDTA | 0.200 g | — |
| ZnCl$_2$ | — | 0.270 g |
| Oxytocin | 0.022 g | 0.022 g |
| HCl | qs | qs |
| NaOH | qs | qs |
| Purified water | 200 ml | 200 ml |
| pH | 5.2 | 4.6 |

Example 2

Solutions were prepared by adding additional ingredients (see Table 2) to 20 ml of stock solution I as prepared in Example 1 (at room temperature). The solutions were stirred until all solids were dissolved. After addition of the ingredients the pH was measured (Table 2).

TABLE 2

| Solution | Ingredient (g) | pH |
|---|---|---|
| 2A | 1 g mannitol | 5.23 |
| 2B | 1 g sucrose + 0.4 g raffinose | 5.24 |
| 2C | 1 g dextran 40 | 5.28 |

10 ml samples of these solutions were freeze dried overnight using a benchtop freeze drier. The freeze dried powder was stored at 2-8° C. In addition, 10 ml samples of these solutions were stored at 2-8° C.

After preparation of all samples, the samples were transferred to accelerated stability testing conditions (40° C./75% RH). The oxytocin concentration was determined in samples taken at the start of the stability testing (t=0) and 1 month later. For sample 2C the oxytocin concentrations were also measured after 2 months of accelerated stability testing. The results of these analyses are shown in Table 3.

TABLE 3

| | Solution Oxytocin % [1] | | Powder Oxytocin % [1] | |
|---|---|---|---|---|
| Sample | 1 month | 2 months | 1 month | 2 months |
| 2A | 56.7 | — | 83.5 | — |
| 2B | 57.0 | — | 80.3 | — |
| 2C | 48.4 | 26.9 | 99.4 | 101.1 |

[1] Concentration calculated as percentage of oxytocin in sample t = 0

Example 3

Solutions were prepared by adding additional ingredients (see Table 4) to 20 ml stock solution II as prepared in example 1 (at room temperature). The solutions were stirred until all solids were dissolved. After addition of the ingredients the pH was measured (Table 4).

TABLE 4

| Solution | Ingredient | pH |
|---|---|---|
| 3A | 1 g mannitol | 4.66 |
| 3B | 1 g dextran 40 | 4.65 |

10 ml samples of these solutions were freeze dried overnight using a bench-top freeze drier. The freeze dried powder was stored at 2-8° C. In addition, 10 ml samples of these solutions were stored at 2-8° C.

After preparation of all samples, the samples were transferred to accelerated stability testing conditions (40° C./75% RH). The oxytocin concentration was determined in samples taken at the start of the stability testing (t=0) and 1 and 2 months later. The results of these analyses are shown in Table 5.

TABLE 5

| | Solution Oxytocin % [1] | | Powder Oxytocin % [1] | |
|---|---|---|---|---|
| Sample | 1 month | 2 months | 1 month | 2 months |
| 3A | 86.2 | 73.4 | 67.8 | 58.7 |
| 3B | 81.9 | 56.4 | 101.6 | 102.4 |

[1] Concentration calculated as percentage of oxytocin in sample t = 0

Example 4

Tablets having a tablet weight of 100 mg were prepared on the basis of the recipe shown in Table 6.

TABLE 6

| Ingredient | Amount (in grams) | Wt. % |
|---|---|---|
| Freeze-dried Oxytocin-Dextran example 2C | 1.27 | 8.8 |
| Prosolv ® HD 90 (Silicified Microcrystalline Cellulose) | 1.81 | 12.5 |
| Pruv ® (sodium stearyl fumarate) | 0.10 | 0.7 |
| Ac-Di-sol ® (croscarmellose sodium) | 1.00 | 6.9 |
| Aspartame | 0.10 | 0.7 |
| Lime flavor | 0.05 | 0.35 |
| F-melt ® (excipient)[1] | 10.20 | 70.20 |

[1] containing mannitol, xylitol, microcrystalline cellulose and crospovidone

The freeze dried powder and the other components were mixed for 15 minutes in a free-fall mixer before being compressed into tablets of 100 mg using an Excenter press. Each tablet contained 16.7 μg of oxytocin or 10 I.U.

Example 5

An oxytocin containing powder was prepared by preparing an aqueous solution having the composition described in Table 7, followed by freeze drying of this solution.

TABLE 7

| Ingredients | |
|---|---|
| Citric acid anhydrate | 0.265 g |
| Sodium citrate dihydrate | 0.805 g |
| Dextran | 2.50 g |
| ZnCl$_2$ | 0.27 g |
| Oxytocin | 0.25 g |
| Distilled water | 200 ml |

The aqueous solution was prepared using water at room temperature (appr. 20° C.) The solid ingredients, except for the oxytocin and dextran, were introduced into a container. Approximately 90% of the required water was added, followed by continuous stirring with a magnetic stirrer until all solids were dissolved. The oxytocin and dextrin were added and the pH of the solution was set with 1M HCl or 1M NaOH to pH 4.6. The remaining amount of water was added and mixed.

The aqueous oxytocin solution was freeze dried overnight using a bench-top freeze drier Next, the freeze dried powder was combined with excipients (lactose, sodium starch glycolate, ascorbic acid, Ludiflash® and sodium stearyl fumarate) to produce the tablet formulation described in Table 8.

TABLE 8

| Ingredients | Wt. % |
|---|---|
| Freeze dried powder | 5.4 |
| Lactose | 35.6 |
| Sodium starch glycolate | 5 |
| Ascorbic acid | 2.5 |
| Ludiflash ® | 50.0 |
| Sodium stearyl fumarate | 1.5 |

The aforementioned tablet formulation was compressed into tablets of 100 mg. Each tablet contained 330 µm (200 I.U.) of oxytocin. Both the coated powder and the tablets can be stored under ambient conditions for several months without a substantial decrease in oxytocin content being observed.

The invention claimed is:

1. An orally disintegrating solid pharmaceutical dosage unit having a weight between 50 and 1,000 mg and comprising:
    (a) 1-100 wt. % of particles comprising:
        (i) 0.01-10 wt. % of a partus control substance selected from oxytocin, carbetocin, and combinations thereof;
        (ii) 5-70 wt. % of buffering agent;
        (iii) 20-94 wt. % of branched glucan;
        (iv) 0-70 wt. % of other pharmaceutically acceptable ingredients; and
    (b) 0-99 wt. % of one or more pharmaceutically acceptable excipients;
    wherein the solid dosage unit comprises at least 5 µg of the partus control substance and has a pH buffer range of 3.5-5.7.

2. The dosage unit according to claim 1, wherein the buffering agent has a pH buffer range of 4.0 to 5.5.

3. The dosage unit according to claim 1, wherein the buffering agent is selected from citrate, acetate, aspartate and combinations thereof.

4. The dosage unit according to claim 1, wherein the branched glucan is hydrolyzed dextran with an average molecular weight in the range of 10-200 kDa.

5. The dosage unit according to claim 1, wherein the partus control substance is oxytocin.

6. The dosage unit according to claim 1, wherein the partus control substance is carbetocin.

7. The dosage unit according to claim 1, wherein the particles contain 0.02-10 wt. % of divalent metal cation.

8. The dosage unit according to claim 7, wherein the divalent metal cation and the partus control substance are present in the particles in a molar ratio between 5:1 and 1000:1.

9. The dosage unit according to claim 8, wherein the divalent metal cation and the partus control substance are present in the particles in a molar ratio between 10:1 and 300:1.

10. The dosage unit according to claim 1, wherein the particles contain 0.01-10 wt. % of a sequestrant.

11. The dosage unit according to claim 1, wherein the one or more pharmaceutically acceptable excipients are selected from lactose, mannitol, xylitol, microcrystalline cellulose, croscarmellose sodium and combinations thereof.

12. A method of medical treatment, comprising buccally, sublingually or sublabially administering a dosage unit according to claim 1.

13. The method according to claim 12, wherein the medical treatment comprises treatment of postpartum haemorrhage.

14. A method of preparing a solid dosage unit according to claim 1, comprising:
    (a) providing an aqueous solution comprising the partus control substance, the buffering agent, branched glucan and optionally one or more other pharmaceutically acceptable ingredients;
    (b) removing water from the aqueous solution, optionally after having sprayed the aqueous solution onto carrier particles, to produce solid particles containing the partus control substance, the buffering agent, the branched glucan and the optional one or more other pharmaceutically acceptable ingredients;
    (c) mixing the particles with the one or more pharmaceutically acceptable excipients; and
    (d) forming the mixture into a solid dosage unit.

* * * * *